US011517521B2

(12) United States Patent
Micka et al.

(10) Patent No.: US 11,517,521 B2
(45) Date of Patent: Dec. 6, 2022

(54) ABUSE DETERRENT IMMEDIATE RELEASE FORMULATIONS COMPRISING NON-CELLULOSE POLYSACCHARIDES

(71) Applicant: SpecGX LLC, Webster Groves, MO (US)

(72) Inventors: Alex Micka, Hazelwood, MO (US); Kai Feng, Hazelwood, MO (US); Tsz Chung Lai, Hazelwood, MO (US); Jonathan Gaik, Hazelwood, MO (US)

(73) Assignee: SpecGX LLC, Webster Groves, MO (US)

( * ) Notice: Subject to any disclaimer, the term of this patent is extended or adjusted under 35 U.S.C. 154(b) by 305 days.

(21) Appl. No.: 16/002,199

(22) Filed: Jun. 7, 2018

(65) Prior Publication Data

US 2018/0296467 A1    Oct. 18, 2018

Related U.S. Application Data

(63) Continuation of application No. 14/788,908, filed on Jul. 1, 2015.

(60) Provisional application No. 62/020,726, filed on Jul. 3, 2014.

(51) Int. Cl.
| | |
|---|---|
| *A61K 31/485* | (2006.01) |
| *A61K 9/20* | (2006.01) |
| *A61K 9/28* | (2006.01) |
| *A61K 9/46* | (2006.01) |
| *A61K 45/06* | (2006.01) |

(52) U.S. Cl.
CPC ............ *A61K 9/0007* (2013.01); *A61K 9/205* (2013.01); *A61K 9/2009* (2013.01); *A61K 9/2013* (2013.01); *A61K 9/2031* (2013.01); *A61K 9/2054* (2013.01); *A61K 9/2095* (2013.01); *A61K 9/2893* (2013.01); *A61K 31/485* (2013.01); *A61K 45/06* (2013.01)

(58) Field of Classification Search
CPC .. A61K 9/0007; A61K 9/2009; A61K 9/2013; A61K 9/205; A61K 9/2054; A61K 9/2095; A61K 9/2893; A61K 31/485; A61K 45/06
See application file for complete search history.

(56) References Cited

U.S. PATENT DOCUMENTS

| | | |
|---|---|---|
| 2,211,485 A | 8/1940 | Zimmermann |
| 3,891,756 A | 6/1975 | Kasugai et al. |
| 3,980,766 A | 9/1976 | Shaw et al. |
| 4,070,494 A | 1/1978 | Hoffmeister et al. |
| 4,678,661 A | 7/1987 | Gergely et al. |
| 4,956,182 A | 9/1990 | Bequette et al. |
| 5,096,714 A | 3/1992 | Kuhrts |
| 5,486,364 A | 1/1996 | King |
| 6,071,539 A | 6/2000 | Robinson |
| 6,200,604 B1 | 3/2001 | Pather et al. |
| 6,264,981 B1 | 7/2001 | Zhang et al. |
| 6,309,668 B1 | 10/2001 | Bastin et al. |
| 6,340,471 B1 | 1/2002 | Kershman et al. |
| 6,541,025 B1 | 4/2003 | Kershman et al. |
| 6,713,089 B1 | 3/2004 | Bertelsen et al. |
| 7,201,920 B2 | 4/2007 | Kumar et al. |
| 7,510,726 B2 | 3/2009 | Kumar et al. |
| 7,658,944 B2 | 2/2010 | Holm et al. |
| 7,776,314 B2 | 8/2010 | Bartholomaus et al. |
| 7,955,619 B2 | 6/2011 | Shah et al. |
| 8,075,872 B2 | 12/2011 | Arkenau-Maric et al. |
| 8,114,383 B2 | 2/2012 | Bartholomaus et al. |
| 8,114,384 B2 | 2/2012 | Arkenau et al. |
| 9,301,918 B2 | 4/2016 | Raman |
| 2003/0049311 A1 | 3/2003 | McAllister |
| 2003/0068375 A1 | 4/2003 | Wright et al. |
| 2004/0005359 A1 | 1/2004 | Cheng et al. |
| 2005/0165038 A1 | 7/2005 | Gordon |
| 2005/0236741 A1 | 10/2005 | Arkenau et al. |
| 2006/0002860 A1 | 1/2006 | Bartholomaus et al. |
| 2006/0193782 A1 | 8/2006 | Bartholomaus et al. |
| 2007/0004795 A1 | 1/2007 | Sesha |
| 2007/0048228 A1 | 3/2007 | Arkenau-Maric et al. |
| 2007/0166234 A1 | 7/2007 | Kumar et al. |
| 2007/0183980 A1 | 8/2007 | Arkenau-Maric et al. |
| 2008/0102121 A1 | 5/2008 | Devane |
| 2008/0247959 A1 | 10/2008 | Bartholomaus et al. |
| 2008/0248113 A1 | 10/2008 | Bartholomaus et al. |
| 2008/0280975 A1 | 11/2008 | Badul |
| 2008/0311187 A1 | 12/2008 | Ashworth et al. |
| 2008/0311205 A1 | 12/2008 | Habib et al. |
| 2009/0081290 A1 | 3/2009 | McKenna et al. |
| 2009/0098200 A1 | 4/2009 | Temtsin Krayz et al. |
| 2009/0124650 A1 | 5/2009 | Ahdieh |
| 2009/0175937 A1 | 7/2009 | Rahmouni et al. |

(Continued)

FOREIGN PATENT DOCUMENTS

| | | |
|---|---|---|
| AU | 2013206525 | 8/2013 |
| BR | 112015021002 A2 | 7/2017 |

(Continued)

OTHER PUBLICATIONS

International Pharmaceutical Excipients Council—Qualification of Excipients for Use in Pharmaceuticals (pp. 1-66, published 2008) (Year: 2008).*

(Continued)

*Primary Examiner* — Alma Pipic

(57) ABSTRACT

The present disclosure provides pharmaceutical compositions that provide immediate release of active ingredients and have abuse deterrent properties. In particular, the pharmaceutical compositions comprise at least one pharmaceutically active ingredient, at least one non-cellulose polysaccharide, at least one hydrophilic gelling polymer, and an effervescent system.

8 Claims, No Drawings

(56) References Cited

U.S. PATENT DOCUMENTS

| | | |
|---|---|---|
| 2009/0196922 A1 | 8/2009 | Guerrero et al. |
| 2009/0205534 A1 | 8/2009 | Sunnucks |
| 2009/0221621 A1 | 9/2009 | Sathyan et al. |
| 2009/0232887 A1 | 9/2009 | Odidi |
| 2009/0317355 A1 | 12/2009 | Roth et al. |
| 2010/0092553 A1 | 4/2010 | Guimberteau et al. |
| 2010/0151028 A1 | 6/2010 | Ashworth et al. |
| 2010/0166858 A1 | 7/2010 | Mehta et al. |
| 2010/0168148 A1 | 7/2010 | Wright et al. |
| 2010/0203130 A1* | 8/2010 | Tygesen |
| 2010/0204259 A1* | 8/2010 | Tygesen |
| 2010/0260833 A1 | 10/2010 | Bartholomaus et al. |
| 2011/0020451 A1 | 1/2011 | Bartholomaus |
| 2011/0038930 A1 | 2/2011 | Barnscheid |
| 2011/0054038 A1 | 3/2011 | Glozman |
| 2011/0077238 A1 | 3/2011 | Leech et al. |
| 2011/0117196 A1 | 5/2011 | Gordon |
| 2011/0136921 A1 | 6/2011 | Dumbre |
| 2011/0165248 A1 | 7/2011 | Machonis |
| 2011/0268666 A1 | 11/2011 | Friedman et al. |
| 2012/0028937 A1 | 2/2012 | Tsuzuki et al. |
| 2012/0135075 A1* | 5/2012 | Mohammad |
| 2012/0136021 A1 | 5/2012 | Barnscheid et al. |
| 2012/0214777 A1 | 8/2012 | Crowley et al. |
| 2012/0321674 A1 | 12/2012 | Vachon et al. |
| 2012/0321716 A1 | 12/2012 | Vachon et al. |
| 2013/0171212 A1 | 7/2013 | Leskovar |
| 2013/0171256 A1 | 7/2013 | Hamed |
| 2013/0209560 A1 | 8/2013 | Hamed |
| 2013/0266660 A1 | 10/2013 | Hamed |
| 2013/0280176 A1 | 10/2013 | Diezi |
| 2013/0280177 A1 | 10/2013 | Raman |
| 2014/0010873 A1 | 1/2014 | Tygesen |
| 2015/0224097 A1 | 8/2015 | Sareen et al. |

FOREIGN PATENT DOCUMENTS

| | | |
|---|---|---|
| EP | 2123274 A1 | 11/2009 |
| EP | 2161021 A1 | 3/2010 |
| JP | 62-089616 | 4/1987 |
| JP | 2011105615 A | 6/2011 |
| MX | 2015012060 A | 1/2016 |
| WO | 0025749 A1 | 5/2000 |
| WO | 2002/019987 A1 | 3/2002 |
| WO | 03/032954 A1 | 4/2003 |
| WO | 03/0333031 A1 | 4/2003 |
| WO | 2006002836 A1 | 1/2006 |
| WO | 2007117605 A2 | 10/2007 |
| WO | 2008/033523 A1 | 3/2008 |
| WO | 2008/039737 A2 | 4/2008 |
| WO | 2008/128191 A2 | 10/2008 |
| WO | 2009/092601 A1 | 7/2009 |
| WO | 2011/066980 A2 | 6/2011 |
| WO | 2011079074 A1 | 6/2011 |
| WO | 2011143118 A2 | 11/2011 |
| WO | 2011143120 A1 | 11/2011 |
| WO | 2012/112952 A1 | 8/2012 |
| WO | 2013/077851 A1 | 5/2013 |
| WO | 2013158810 A1 | 10/2013 |
| WO | 2013158814 A1 | 10/2013 |
| WO | 2014047731 A1 | 4/2014 |
| WO | 2014152296 A1 | 9/2014 |
| WO | 2016004170 A1 | 1/2016 |

OTHER PUBLICATIONS

International Preliminary Report on Patentability dated Oct. 21, 2014 from related International application No. Pcti US2013/037046, 7 pgs.

International Preliminary Report on Patentability dated Oct. 21, 2014 from related International application No. PCT/US2013/037056, 6 pgs.

International Search Report and Written Opinion dated Jul. 10, 2014 from related International application No. PCT/US2014/027176, 10 pgs.

Office action dated Apr. 13, 2015 from related U.S. Appl. No. 13/865,286, 16 pgs.

Office action dated Sep. 15, 2014 from related U.S. Appl. No. 13/865,286, 13 pgs.

Beer Beate, "Impact of slow-release oral morphine on drug abusing habits in Austria", Neuropsychiatrie, Dustri Verlag, Deisenhofen, DE, vol. 24, No. 2, Jan. 1, 2010, pp. 108-117.

Born, Chapter 11 "Xanthan", 2002, pp. 259-269, downloaded from the internet at URL <http://www.wiley-vch.do/books/biopoly/pdf_v09/bpol5011_259_269.pdf>.

Polyox water soluble resins brochure, 2002, 24 pgs., downloaded from the internet from URL <http://msdssearch.dow.com/PublishedLiteratureDOWCOM/dh_0031/0901b80380031a4a.pdf?filepath=/326-00001.pdf&fromPage=GetDoc>.

Office action dated Oct. 7, 2015 from related U.S. Appl. No. 12/865,244, 9 pgs.

Office action dated Feb. 3, 2016 from related U.S. Appl. No. 13/865,286, 14 pgs.

Office action dated Aug. 19, 2015 from related U.S. Appl. No. 14/211,307, 10 pgs.

International Search Report and Written Opinion dated Oct. 6, 2015 from related international application No. PCT/US2015/038774, 8 pgs.

Office action dated Mar. 10, 2015 from related U.S. Appl. No. 14/211,307, 5 pgs.

Monso-San De, Glucomannan, a promising polysaccharide for biopharmaceutical purposes, European Journal of Pharmaceutics and Biopharmaceutics, 2009, vol. 72, 453-462.

Lubrizol Technical Data Sheet, Molecular Weight of Carbopol and Pemulen Polymers, TDS-222, Oct. 15, 2007, 3 pgs.

OPADRY // High Performance Film Coating system, The Effect of coating Process Conditions and Coating formula Type on the Quantity and Location of Water in Film Coated Tablets, colorcon, 2009, 5 pgs.

USUI, Interactions in the Solid State I: Interactionsof Sodium Bicarbonate and Tartaric Acid Under Compressed Conditions, Journal of Pharmaceutical Sciences, Dec. 1985, 74(12), 1293-1297.

Search report dated Nov. 7, 2017 from related European Application No. 15815497.1, 7 pp.

Bhatt et al., "Pharmaceutical Engineering: Mixing," 2007, pp. 1-24, <nsdl.niscair.res.in/jspui/bitstream/123456789/751/1/Revised%20mixing.pdf>.

Final Office action dated May 5, 2017 from related U.S. Appl. No. 13/865,286, 8 pp.

Notice of Allowance dated Aug. 7, 2017 from related U.S. Appl. No. 13/865,286, 14 pp.

Final Office action dated Jun. 16, 2017 from related U.S. Appl. No. 13/865,244, 9 pp.

Jun. 1, 2017 Letter from Associate regarding Mexican Office action dated May 28, 2017, 3 pp.

Shah, "Polyox (Polyethylene Oxide) Multifunctional Polymer in Novel Drug Delivery System." Int. J. Pharmaceut Sci. and Drug Res., 2014, 6(2):95-101.

Office action dated Feb. 19, 2016 from related CA Application No. 2,864,738, 5 pgs.

Office action dated Mar. 7, 2016 from related JP Application No. 2015-507160, 11 pgs.

Office action dated May 20, 2016 from related U.S. Appl. No. 13/865,244, 10 pgs.

Office action dated Apr. 20, 2016 from related JP Application No. 2015-507158, 12 pgs.

Notice of Allowance dated Jan. 12, 2017 from related CA Application No. 2,864,738, 1 pg.

Notice of Allowance dated Feb. 22, 2017 from related JP Application No. 2015-507158, 5 pgs.

Intent to Grant dated Mar. 9, 2017 from related EP Application No. 13719340.5, 62 pgs.

Apr. 2, 2017 Letter from IL associate regarding Office action dated Feb. 13, 2017 from related IL Application No. 234996, 2 pgs.

Apr. 4, 2017 Letter from IL associate regarding Office action dated Feb. 19, 2017 from related IL Application No. 234997, 3 pgs.

(56) References Cited

OTHER PUBLICATIONS

Office action dated Jul. 5, 2016 from related CA Application No. 2,868,416, 4 pgs.
Office action dated Jul. 12, 2016 from related JP Application No. 2015-507160, 7 pgs.
Office action dated Oct. 19, 2016 from related JP Application No. 2015-507158, 7 pgs.
Office action dated Nov. 9, 2016 from related EP Application No. 13719672.1, 6 pgs.
Dec. 8, 2016 Letter from JP associate regarding Notice of Allowance dated Dec. 8, 2016 from related JP Application No. 2015-507160, 6 pgs.
Office action dated Sep. 22, 2016 from related U.S. Appl. No. 13/865,286, 6 pgs.
Office action dated Dec. 1, 2016 from related U.S. Appl. No. 13/865,244, 10 pgs.
Communication under Rule 71(3) EPC dated Aug. 5, 2018 from related EP Application 13719672.1, 7 pgs.
Communication from IL associate dated Jun. 27, 2018 re Office Action dated May 30, 2018 from related IL National Application No. 234997, 2 pgs.
Communication from MX associated dated May 8, 2018 re Notice of Allowance dated Apr. 29, 2018 from related MX National Application No. MX/a/2014/009876, 2 pgs.
Final Office action dated Mar. 28, 2019 from related U.S. Appl. No. 14/788,908, 13 pp.
Office action dated Oct. 3, 2018 from related U.S. Appl. No. 14/788,908, 19 pp.
Final Office action dated May 9, 2018 from related U.S. Appl. No. 14/788,908, 16 pp.
Office action dated Jan. 8, 2018 from related U.S. Appl. No. 14/788,908, 17 pp.
Final Office action dated Sep. 25, 2017 from related U.S. Appl. No. 14/788,908, 14 pp.
Office action dated May 16, 2017 from related U.S. Appl. No. 14/788,908, 15 pp.
Final Office action dated Jan. 19, 2017 from related U.S. Appl. No. 14/788,908, 21 pp.
Office action dated Jul. 21, 2016 from related U.S. Appl. No. 14/788,908, 16 pp.
Final Office action dated Mar. 15, 2016 from related U.S. Appl. No. 14/788,908, 26 pp.
Office action dated Nov. 24, 2015 from related U.S. Appl. No. 14/788,908, 9 pp.
Office action dated May 16, 2019 from related European Application No. 15815497.1, 5 pp.
Office action dated Dec. 19, 2018 from related Japanese Application No. 2016-575456, 12 pp.
Office action dated Dec. 13, 2018 from related U.S. Appl. No. 15/714,137, 14 pp.
Office action dated Jun. 13, 2019 from related U.S. Appl. No. 15/714,137, 12 pp.
Office action dated Apr. 5, 2019 from related U.S. Appl. No. 15/977,415, 13 pp.
Office action dated Apr. 5, 2019 from related U.S. Appl. No. 16/002,190, 15 pp.
Patil, Hot-Melt Extrusion: from Theory to Application in Pharmaceutical Formulation, AAPS PharmSciTech, Feb. 2016, vol. 17, No. 1, 23 pp.
Office action dated Oct. 30, 2019 from related U.S. Appl. No. 14/788,908, 13 pp.
Office action dated Oct. 25, 2019 from related U.S. Appl. No. 15/977,415, 11 pp.
Office action dated Sep. 6, 2019 from related Australia Application No. 2015284078, 5 pp.
Office action dated Oct. 24, 2019 from related Japanese Application No. 2016-575456, 8 pp.
Office action dated Nov. 23, 2019 from related Mexican Application No. MX/a/2017/000041, 5 pp.
Office action dated Oct. 29, 2019from related U.S. Appl. No. 16/002,190, 11 pp.
Bhowmik D., et al., "Controlled Release Drug Delivery Systems," The Pharma Innovation Journal, 2012, vol. 1 (10), pp. 24-32.
Communication pursuant to Article 94(3) for European Patent Application No. EP15815497.1, dated Sep. 16, 2021, 3 Pages.
English Translation of Office Action for Japanese Application No. 2016-575456, dated Dec. 19, 2018, 7 pages.
English Translation of Office Action for Japanese Application No. 2016-575456, dated Jun. 10, 2020, 5 pages.
Final Office Action for U.S. Appl. No. 15/714,137, dated Jul. 24, 2020, 12 pages.
Final Office Action for U.S. Appl. No. 16/002,190, dated Dec. 4, 2020, 23 pages.
Final Office Action for U.S. Appl. No. 16/002,199, dated Jul. 2, 2020, 21 pages.
Final Office Action for U.S. Appl. No. 16/002,199, dated Nov. 29, 2018, 15 pages.
International Preliminary Report on Patentability for International Application No. PCT/US2015/038774, dated Jan. 12, 2017, 06 Pages.
Katzbauer B., "Properties and Applications of Xanthan Gum," Polymer Degradation and Stability, 1998, vol. 59, pp. 81-84.
Non-Final Office Action for U.S. Appl. No. 15/714,137, dated Feb. 23, 2021, 18 pages.
Non-Final Office Action for U.S. Appl. No. 15/714,137, dated Jan. 10, 2020, 12 pages.
Non-Final Office Action for U.S. Appl. No. 16/002,190, dated Jun. 2, 2020, 14 pages.
Non-Final Office Action for U.S. Appl. No. 16/002,199, dated Apr. 2, 2019, 15 pages.
Non-Final Office Action for U.S. Appl. No. 16/002,199, dated Jan. 8, 2020, 18 pages.
Non-Final Office Action for U.S. Appl. No. 16/002,199, dated Jul. 27, 2018, 13 pages.
Notice of Acceptance for Australian Application No. 2015284078, dated Jan. 15, 2020, 3 pages.
Office Action for Mexican Application No. MX/a/2017/000041, dated Jul. 22, 2019, 4 pages.
Office Action for Mexican Application No. MX/a/2017/000041, dated Oct. 17, 2019, 4 pages.
Rowe R.C., et al., "Polyethylene Oxide, Handbook of Pharmaceutical Excipients," Sixth edition, Pharmaceutical Press, 2009, pp. 522-524.
Rowe R.C., et al., "Xanthan Gum, Handbook of Pharmaceutical Excipients," Sixth edition, Pharmaceutical Press, 2009, pp. 782-785.
Advisory Action for U.S. Appl. No. 14/788,908, dated Mar. 30, 2017, 3 Pages.
Examination Report No. 1 for Australian Patent Application No. 2015284078 dated Sep. 6, 2019, 5 Pages.
Final Office Action for U.S. Appl. No. 14/788,908 dated Jun. 11, 2021, 24 Pages.
Final Office Action for U.S. Appl. No. 14/788,908 dated Mar. 6, 2020, 19 Pages.
Non-Final Office Action for U.S. Appl. No. 14/788,908 dated Sep. 25, 2020, 21 pages.
Non-Final Office Action for U.S. Appl. No. 16/990,711 dated Mar. 28, 2022, 23 pages.
Office Action for Canadian Patent Application No. 2953396, dated May 27, 2021, 5 Pages.
Office Action for Japanese Patent Application No. 2016575456, dated Jun. 10, 2020, 10 Pages.
Office Action for Japanese Patent Application No. 2016575456, dated Oct. 13, 2020, 9 Pages.
Office Action for Japanese Patent Application No. 2016575456, dated Oct. 29, 2019, 15 Pages.
Office action for Mexican Application No. MX/a/2017/000041 dated Jul. 13, 2020, 9 pages.
Office action for Mexican Application No. MX/a/2017/000041 dated Nov. 20, 2020, 13 pages.

(56) References Cited

OTHER PUBLICATIONS

Office Action from Brazilian Patent Application No. BR112016030648-1, dated Jun. 19, 2020, 9 pages.

\* cited by examiner

ABUSE DETERRENT IMMEDIATE RELEASE FORMULATIONS COMPRISING NON-CELLULOSE POLYSACCHARIDES

CROSS-REFERENCE TO RELATED APPLICATIONS

This application is a continuation of U.S. application Ser. No. 14/788,908, filed Jul. 1, 2015, which claims the benefit of U.S. Provisional Application Ser. No. 62/020,726, filed Jul. 3, 2014, the disclosure of each is hereby incorporated by reference in its entirety.

FIELD

The present disclosure generally relates to pharmaceutical compositions that provide immediate release of active ingredients and have abuse deterrent properties.

BACKGROUND

Abuse of prescription drugs (particularly opioids) has become a serious societal problem. Such abuse places an enormous economic burden on society due to increased health care, work place, and criminal justice costs. Several routes of administration are commonly attempted by abusers. For example, the oral solid dosage form may be crushed or pulverized into a powder and administered intranasally (i.e., snorted) or dissolved in a suitable solvent (e.g., water) and administered parenterally (i.e., injected intravenously).

Attempts have been made to diminish the abuse of opioid solid dosage forms. One approach has been to include in the dosage form an opioid antagonist that is not orally active but will substantially block the analgesic effects of the opioid if one attempts to dissolve the opioid and administer it parenterally. Another approach has been to include gel-forming high molecular weight polymers that confer plasticity to the dosage form rendering them difficult to crush and pulverize into a powder. These high molecular weight polymers, however, retard the release of the active ingredient from the dosage forms, making them unsuitable for immediate release formulations.

Thus, there is a need for oral solid dosage forms that provide immediate release of the active ingredient yet are resistant to abuse.

SUMMARY

Among the various aspects of the present disclosure is a pharmaceutical composition comprising at least one active pharmaceutical ingredient (API) or a pharmaceutically acceptable salt thereof, at least one non-cellulose polysaccharide, at least one hydrophilic gelling polymer, and an effervescent system.

A further aspect of the present disclosure encompasses an abuse deterrent solid dosage form comprising at least one active pharmaceutical ingredient (API) susceptible to abuse or a pharmaceutically acceptable salt thereof, at least one natural gum, at least one hydrophilic gelling polymer, and an effervescent system.

Other aspects and iterations of the disclosure are described in more detail below.

DETAILED DESCRIPTION

The present disclosure provides pharmaceutical compositions that provide rapid release of the active ingredients and have abuse deterrent properties. In particular, the pharmaceutical compositions comprise non-cellulose polysaccharides and hydrophilic gelling polymers in combination with an effervescent system comprising an acid component and a base component. It was unexpectedly discovered that the combination of non-cellulose polysaccharides, hydrophilic gelling polymers, and the effervescent system makes the compositions resistant to crushing into fine powders and/or extracting with suitable solvents at a variety of temperatures, while still providing immediate release of the active ingredient(s). The present disclosure also provides processes for preparing the immediate release, abuse deterrent pharmaceutical compositions disclosed herein.

(I) Pharmaceutical Compositions

One aspect of the present disclosure provides abuse deterrent pharmaceutical compositions that provide immediate release of the active pharmaceutical ingredients. Detailed below are the components of the compositions, release characteristics of the compositions, and abuse deterrent properties of the compositions.

(a) Components

The pharmaceutical compositions disclosed herein comprise at least one non-cellulose polysaccharide, at least one hydrophilic gelling polymer, and an effervescent system. The combination of the non-cellulose polysaccharide, the hydrophilic gelling polymers, and the effervescent system yields a composition that has abuse deterrent properties (e.g., is difficult to crush into a fine powder or extract with an aqueous solvent) but which also provides rapid and immediate release of the active ingredient.

(i) Non-Cellulose Polysaccharides

A variety of non-cellulose polysaccharides may be included in the pharmaceutical compositions disclosed herein. Suitable polysaccharides include, without limit, natural gums, hemicelluloses (such as xyloglucans, xylans, and mannans), pectins (e.g., derived from citrus, apples, pears gooseberries, and the like), chitins, starches (e.g., derived from corn, potato, rice, and so forth), glycogen, chrysolaminarin, derivatives thereof, and combinations thereof.

In certain embodiments, the non-cellulose polysaccharide is a natural gum or a combination of natural gums. Natural gums are non-cellulose polysaccharides derived from botanical sources, seaweeds, or produced via bacterial fermentation. Non-limiting examples of plant-derived natural gums include albizia gum, aloe mucilage, beta-glucan, chicle gum, dammar gum, fenugreek gum, glucomannan, guar gum, gum arabic (also called acacia gum), gum copal, gum ghatti, gum tragacanth, hakea gum, Hibiscus rosasinensis gum, honey locust gum, hupu gum, karaya gum, khaya gum, *Lepidium sativum* gum, locust bean gum, mastic gum, *Mimosa scabrella* gum, *Mimosa pudica* gum, okra gum, psyllium seed husks (also called ispaghula husk), spruce gum, *Sterculia foetida* gum, tamarind gum, tara gum, and derivatives of any of the foregoing. Examples of natural gums derived from seaweeds include, without limit, alginate or alginic acid, fucoidan, and laminarin derived from brown seaweeds, and agar and carrageenans derived from red seaweeds. Non-limiting examples of natural gums produced by bacterial fermentation include xanthan gum, gellan gum, dextran, welan gum, diutan gum, pullulan, and derivatives thereof.

In specific embodiments, the non-cellulose polysaccharide is a natural gum. In one embodiment, the non-cellulose polysaccharide may be a glucomannan. Glucomannans are linear polysaccharides composed of β-1,4 linked D-mannose and D-glucose residues (with acetyl side branches on some of the backbone units) that are derived from softwoods, roots, tubers, and plant bulbs. The mannose to glucose ratio depends upon the source of the glucomannan. For example, konjac glucomannan, which is derived from the tubers of *Amorphophallus konjac* K. Koch, has a mannose:glucose ratio of 1.6:1, whereas those extracted from Scotch pine or orchids have ratios of 2.1:1 or 3.6:1, respectively. In a particular iteration, the glucomannan may be konjac glucomannan. In another embodiment, the non-cellulose polysaccharide may be a combination of glucomannan and xanthan gum.

In general, the non-cellulose polysaccharide has a high molecular weight and forms a viscous mixture or gel upon contact with water or an aqueous solution. In some embodiments, the polysaccharide may have an average molecular weight of greater than about 200,000, greater than about 500,000, greater than about 1,000,000, greater than about 2,000,000, or greater than about 4,000,000.

The amount of the non-cellulose polysaccharide present in the pharmaceutical composition, can and will vary depending upon the desired properties of the pharmaceutical composition, as well as the identity and amounts of other components present in the dosage form. In general, the amount of non-cellulose polysaccharide in the composition may range from about 2% to about 60% by weight of the pharmaceutical composition. In various embodiments, the amount of the non-cellulose polysaccharide may range from about 3% to about 50%, from about 5% to about 40%, from about 6% to about 30%, or from about 10% to about 25% by weight of the pharmaceutical composition. In some embodiments, the amount of non-cellulose polysaccharide may range from 2% to about 10%, from about 10% to about 15%, from about 15% to about 20%, from about 20% to about 25%, from about 25% to about 40%, or from about 40% to about 60% by weight of the pharmaceutical composition. In particular embodiments, the amount of non-cellulose polysaccharide may be about 25% or less by weight of the pharmaceutical composition. In specific embodiments, the amount of non-cellulose polysaccharide in the composition may range from about 5% to about 40% by weight of the pharmaceutical composition.

(ii) Hydrophilic Gelling Polymers

The pharmaceutical compositions disclosed herein also comprise at least one hydrophilic gelling polymer. The term "hydrophilic gelling polymer" refers to a polymer with affinity for water such that it readily absorbs water or an aqueous solution and/or swells when in contact with water or an aqueous solution to form a viscous mixture or gel.

A variety of hydrophilic gelling polymers are suitable for use in the pharmaceutical solid dosage forms. The polymer may be natural, semi-synthetic, or synthetic. Non-limiting examples of suitable hydrophilic gelling polymers include cellulose ethers, polyalkylene oxides, polyacrylic acids, polyamines, polyolefinic alcohols, polyvinyl lactams, derivatives thereof, and combinations thereof.

In some embodiments, the hydrophilic gelling polymer may be a cellulose ether. Cellulose ethers are cellulose derivatives in which the hydrogen atoms of hydroxyl groups are replaced with alkyl groups. The degree of substitution can and will vary. Non-limiting examples of suitable cellulose ethers include hydroxypropylcellulose (HPC), hydroxypropylmethylcellulose (HPMC), carboxymethylcellulose (CMC) (e.g., sodium carboxymethylcellulose), methylcellulose, hydroxyethylcellulose, hydroxyethylmethylcellulose, methylhydroxyethylcellulose, and the like. In specific embodiments, the cellulose ether may be hydroxypropylcellulose, hydroxypropylmethylcellulose, sodium carboxymethylcellulose, or combinations thereof. The average molecular weight of the cellulose ether may range from about 20,000 to about 1,500,000. In various embodiments, the weight average molecular weight of the cellulose ether may be about 30,000, about 100,000, about 250,000, about 850,000, or about 1,150,000.

In other embodiments, the hydrophilic gelling polymer may be a polyalkylene oxide such as polyethylene oxide (PEO), polypropylene oxide (PPO), derivatives thereof, copolymers thereof, or combinations thereof. In particular embodiments, the hydrophilic gelling polymer may be a polyethylene oxide or a combination of polyethylene oxides of different molecular weights. The average molecular weight of the polyethylene oxide may range from about 100,000 to about 10,000,000. In certain embodiments, the polyethylene oxide may have an average molecular weight of about 100,000 or about 4,000,000.

In still other embodiments, the hydrophilic polymer may be a polyacrylic acid. Suitable polyacrylic acids include carbomers, which are homopolymers of acrylic acid cross linked with polyalcohol allyl ethers (e.g., allyl ether pentaerythritol, allyl ether of sucrose, or allyl ether of propylene), and polycarbophil, which is a homopolymer of acrylic acid cross linked with divinyl glycol. Available carbomers include Carbopol 910, 934, 940, 941, and 943P (the codes are indicators of molecular weight and the specific components of the polymer).

In additional embodiments, the hydrophilic gelling polymer may be a polyamine such as polyethyleneimine, polyvinylamine, or the like. In still further embodiments, the hydrophilic gelling polymer may be a polyolefinic alcohol (such as polyvinyl alcohol), or a polyvinyl lactam (such as, e.g., polyvinylpyrrolidone, polyvinyl caprolactam, and the like). The average molecular weight of said polymers may range from about 20,000 to about 1,300,000.

In specific embodiments, the hydrophilic gelling polymer may comprise a combination of one or more cellulose ethers (e.g., hydroxypropylcellulose, hydroxypropylmethylcellulose, sodium carboxymethylcellulose) and one or more polyethylene oxides having different molecular weights.

The amount of the hydrophilic gelling polymer present in the pharmaceutical composition can and will vary depending upon the desired properties of the pharmaceutical composition, as well as the identity and amounts of other components present in the pharmaceutical composition. In general, the amount of the hydrophilic gelling polymer may range from about 5% to about 80% by weight of the pharmaceutical composition. In various embodiments, the amount of the hydrophilic gelling polymer in the composition may range from about 6% to about 70%, from about 8% to about 60%, from about 10% to about 50%, from about 15% to about 40%, or from about 20% to about 35% by weight of the pharmaceutical composition. In certain embodiments, the amount of the hydrophilic gelling polymer may range from about 5% to about 20%, from about 20% to about 25%, from about 25% to about 30%, from about 30% to about 40%, from about 40% to about 60%, or from about 60% to about 80% by weight of the pharmaceutical composition. In specific embodiments, the amount of the hydrophilic gelling polymer may range from about 10% to about 50% by weight of the pharmaceutical composition.

(iii) Effervescent System

The pharmaceutical composition disclosed herein also comprises an effervescent system. As used herein, an "effervescent system" refers to a system generally comprising an acid component and a base component, wherein the system liberates carbon dioxide upon contact with an aqueous solution. Without being bound by any particular theory, it is believed that the effervescent system facilitates rapid dissolution of the API from the composition comprising the combination of non-cellulose polysaccharide(s) and hydrophilic gelling polymer(s).

The acid component of the effervescent system may be an organic acid, an inorganic acid, or a combination thereof. Non-limiting examples of suitable acids include adipic acid, ascorbic acid, benzoic acid, citric acid, fumaric acid, glutaric acid, lactic acid, lauric acid, malic acid, maleic acid, malonic acid, oxalic acid, phthalic acid, sorbic acid, succinic acid, tartaric acid, ammonium phosphate, potassium bitartrate, potassium phosphate, dipotassium phosphate, disodium pyrophosphate, sodium acid pyrophosphate, sodium phosphate, disodium phosphate, and combinations thereof. In specific embodiments, the acid component of the effervescent system may be an organic acid. In one iteration, the acid component may be tartaric acid. In other embodiments, the acid component of the effervescent system may be an inorganic acid.

In some embodiments, the acid component of the effervescent system may be co-processed with a polyalkylene glycol (such as, e.g., polyethylene glycol), a poloxamer (which is a difunctional, tri-block copolymer of polyethylene oxide and polypropylene oxide), or combinations thereof. Non-limiting examples of suitable polyethylene glycols (PEG) include PEG 1000, PEG 2000, PEG 3300, PEG 4000, PEG 5000, PEG 6000, PEG 8000, PEG 10,000, PEG 20,000, PEG 30,000, derivatives thereof, copolymers thereof, and combinations thereof. Examples of suitable polaxamers (which are available under the trade names KOLLIPHOR™ or PLURONIC®) include, without limit, Poloxamer 101, 105, 108, 122, 123, 124, 181, 182, 183, 184, 185, 188, 212, 215, 217, 231, 234, 235, 237, 238, 282, 284, 288, 331, 333, 334, 335, 338, 401, 402, 403, and 407, wherein the first two digits multiplied by 100 give the approximate molecular mass and the last digit multiplied by 10 gives the percentage of the polyoxyethylene oxide content. The acid and the polyalkylene glycol and/or poloxamer may be co-processed by a variety of means including, without limit, hot melt granulation, fluidized hot melt granulation, hot melt mixing, wet granulation, liquid spray mixing, and the like. The amount of polyalkylene glycol and/or poloxamer co-processed with the acid can and will vary. In general, the weight to weight ratio of the acid to the polyalkylene glycol and/or poloxamer may range from about 1:0.01 to about 1:0.5.

The base component of the effervescent system may be a bicarbonate, a carbonate, or a combination thereof. In various embodiments, the base may be an alkali metal bicarbonate, an alkaline earth metal bicarbonate, an alkali metal carbonate, an organic carbonate, or combinations thereof. Non-limiting examples of suitable bases include ammonium bicarbonate, calcium bicarbonate, lithium bicarbonate, magnesium bicarbonate, potassium bicarbonate, sodium bicarbonate, arginine carbonate, ammonium carbonate, calcium carbonate, lysine carbonate, potassium magnesium carbonate, sodium carbonate, sodium glycine carbonate, sodium sesquicarbonate, zinc carbonate, and combinations thereof. In exemplary embodiments, the base may be an alkali metal bicarbonate. In one exemplary embodiment, the base may be sodium bicarbonate. In another exemplary embodiment, the base may be heat-treated sodium bicarbonate (for example EfferSoda® 12).

The mole to mole ratio of the acid component to the base component in the effervescent system may also vary depending, for example, upon the identity of the acid and the base. In general, the mole to mole ratio of the acid component to the base component in the effervescent system may range from about 1:0.2 to about 1:5. For example, the mole to mole ratio of the acid component to the base component in the effervescent system may be about 1:0.2, about 1:0.25, about 1:0.33, about 1:0.5, about 1:1, about 1:2, about 1:3, about 1:4, about 1:5 or any ratio in between. In one exemplary embodiment, the mole to mole ratio of the acid component to the base component in the effervescent system may range from about 1:1 to about 1:3. In another exemplary embodiment, the mole to mole ratio of the acid component to the base component in the effervescent system may be about 1:2.

The amount of the effervescent system present in the pharmaceutical composition can and will vary depending upon the identity of the other components and the desired properties of the pharmaceutical composition. In general, the amount of the effervescent system may range from about 20% to about 90% by weight of the pharmaceutical composition. In various embodiments, the amount of the effervescent system in the composition may range from about 20% to about 80%, from about 25% to about 70%, from about 30% to about 60%, or from about 40% to about 50% by weight of the pharmaceutical composition. In certain embodiments, the amount of the effervescent system may range from about 20% to about 30%, from about 30% to about 40%, from about 40% to about 50%, from about 50% to about 60%, from about 60% to about 70%, from about 70% to about 80%, or from about 80% to about 90% by weight of the pharmaceutical composition. In specific embodiments, the amount of the effervescent system may range from about 30% to about 60% by weight of the pharmaceutical composition.

(iv) Additional Components

In some embodiments, the pharmaceutical composition disclosed herein may also comprise a lubricant. Non-limiting examples of suitable lubricants include metal stearate such as magnesium stearate, calcium stearate, zinc stearate, a polyethylene glycol, a poloxamer, colloidal silicon dioxide, glyceryl behenate, light mineral oil, hydrogenated vegetable oils, magnesium lauryl sulfate, magnesium trisilicate, polyoxyethylene monostearate, sodium stearoyl fumarate, sodium stearyl fumarate, sodium benzoate, sodium lauryl sulfate, stearic acid, sterotex, talc, and combinations thereof. In specific embodiments, the lubricant may be a metal stearate. In one iteration, the lubricant may be magnesium stearate.

The amount of lubricant present in the pharmaceutical composition can and will vary depending upon the identities and amounts of other components in the composition. In embodiments in which a lubricant is present, the amount of lubricant generally ranges from about 0.1% to about 3% by weight of the pharmaceutical composition. In various embodiments, the amount of lubricant present in the composition may range from about 0.1% to about 0.3%, from about 0.3 to about 1%, or from about 1% to about 3% by weight of the composition. In specific embodiments, the amount of lubricant present in the composition may range from about 0.2% to about 2% by weight of the pharmaceutical composition. In one specific embodiment, the amount of lubricant present in the composition may range from about 0.3% to about 1% by weight of the pharmaceutical composition.

In additional embodiments, the pharmaceutical composition disclosed herein may also comprise a preservative. Non limiting examples of suitable preservatives include antioxidants (such as, e.g., alpha-tocopherol, ascorbyl palmitate, butylated hydroxyanisole, butylated hydroxytoluene, citric acid, dihydroguaretic acid, potassium ascorbate, potassium sorbate, propylgallate, sodium bisulfate, sodium isoascorbate, sodium metabisulfate, sorbic acid, 4-chloro-2,6-ditertiarybutylphenol, and so forth), antimicrobials (such as, e.g., benzyl alcohol, cetylpryidine chloride, glycerine, parabens, propylene glycol, potassium sorbate, sodium benzoate, sorbic acid, sodium propionate, and the like), and combinations thereof. In specific embodiments, the preservative may be butylated hydroxytoluene, citric acid, or a combination thereof.

The amount of preservative present in the pharmaceutical composition can and will vary. In embodiments in which a preservative is present, the amount of preservative in the composition may range from about 0.005% to about 3% by weight of the pharmaceutical composition. In various embodiments, the amount of preservative may range from about 0.005% to about 0.03%, from about 0.03 to about 0.1%, from about 0.1% to about 0.3%, from about 0.3% to about 1.0%, or from about 1% to about 3% by weight of the composition. In specific embodiments, the amount of preservative may range from about 0.01% to about 1% by weight of the pharmaceutical composition.

(v) API

The pharmaceutical composition disclosed herein comprises at least one API or a pharmaceutically acceptable salt thereof. Suitable APIs include, without limit, opioid analgesic agents (e.g., adulmine, alfentanil, allocryptopine, allylprodine, alphaprodine, anileridine, aporphine, benzylmorphine, berberine, bicuculine, bicucine, beziramide, buprenorphine, bulbocaprine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphine, nalmefene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tapentadol, tilidine, and tramadol); opioid antagonists (e.g., naloxone, naltrexone, alvimopan, cyprodime, diprenorphine, gemazocine, 5'-guanidinonaltrindole, levallorphan, methylnaltrexone, naldemedine, nalmexone, nalorphine, naloxazone, naloxol, naloxonazine, 6β-naltrexol-d4, naltriben, naltrindole, norbinaltorphimine, oxilorphan, quadazocine, and samidorphan); non-opioid analgesic agents (e.g., acetylsalicylic acid, acetaminophen, paracetamol, ibuprofen, ketoprofen, indomethacin, diflunisol, naproxen, ketorolac, dichlophenac, tolmetin, sulindac, phenacetin, piroxicam, and mefamanic acid); anti-inflammatory agents (e.g., glucocorticoids such as alclometasone, fluocinonide, methylprednisolone, triamcinolone and dexamethasone; non-steroidal anti-inflammatory agents such as celecoxib, deracoxib, ketoprofen, lumiracoxib, meloxicam, parecoxib, rofecoxib, and valdecoxib); antitussive agents (e.g., dextromethorphan, codeine, hydrocodone, caramiphen, carbetapentane, and dextromethorphan); antipyretic agents (e.g., acetylsalicylic acid and acetaminophen); antibiotic agents (e.g., aminoglycosides such as, amikacin, gentamicin, kanamycin, neomycin, netilmicin, streptomycin, and tobramycin; carbecephem such as loracarbef; carbapenems such as certapenem, imipenem, and meropenem; cephalosporins such as cefadroxil cefazolin, cephalexin, cefaclor, cefamandole, cephalexin, cefoxitin, cefprozil, cefuroxime, cefixime, cefdinir, cefditoren, cefoperazone, cefotaxime, cefpodoxime, ceftazidime, ceftibuten, ceftizoxime, and ceftriaxone; macrolides such as azithromycin, clarithromycin, dirithromycin, erythromycin, and troleandomycin; monobactam; penicillins such as amoxicillin, ampicillin, carbenicillin, cloxacillin, dicloxacillin, nafcillin, oxacillin, penicillin G, penicillin V, piperacillin, and ticarcillin; polypeptides such as bacitracin, colistin, and polymyxin B; quinolones such as ciprofloxacin, enoxacin, gatifloxacin, levofloxacin, lomefloxacin, moxifloxacin, norfloxacin, ofloxacin, and trovafloxacin; sulfonamides such as mafenide, sulfacetamide, sulfamethizole, sulfasalazine, sulfisoxazole, and trimethoprim-sulfamethoxazole; tetracyclines such as demeclocycline, doxycycline, minocycline, and oxytetracycline); antimicrobial agents (e.g., ketoconazole, amoxicillin, cephalexin, miconazole, econazole, acyclovir, and nelfinavir); antiviral agents (e.g., acyclovir, gangciclovir, oseltamivir, and relenza); steroids (e.g., estradiol, testosterone, cortisol, aldosterone, prednisone, and cortisone); amphetamine stimulant agents (e.g., amphetamine and amphetamine-like drugs); non-amphetamine stimulant agents (e.g., methylphenidate, nicotine, and caffeine); laxative agents (e.g., bisacodyl, casanthranol, senna, and castor oil); anti-nausea agents (e.g., dolasetron, granisetron, ondansetron, tropisetron, meclizine, and cyclizine); anorexic agents (e.g., fenfluramine, dexfenfluramine, mazindol, phentermine, and aminorex); antihistaminic agents (e.g., phencarol, cetirizine, cinnarizine, ethamidindole, azatadine, brompheniramine, hydroxyzine, and chlorpheniramine); antiasthmatic agents (e.g., zileuton, montelukast, omalizumab, fluticasone, and zafirlukast); antidiuretic agents (e.g., desmopressin, vasopressin, and lypressin); antimigraine agents (e.g., naratriptan, frovatriptan, eletriptan, dihydroergotamine, zolmitriptan, almotriptan, and sumatriptan); antispasmodic agents (e.g., dicyclomine, hyoscyamine, and peppermint oil); antidiabetic agents (e.g., methformin, acarbose, miglitol, pioglitazone, rosiglitazone, nateglinide, repaglinide, mitiglinide, saxagliptin, sitagliptine, vildagliptin, acetohexamide, chlorpropamide, gliclazide, glimepiride, glipizide, glyburide, tolazamide, and tolbutamide); respiratory agents (e.g., albuterol, ephedrine, metaproterenol, and terbutaline); sympathomimetic agents (e.g., pseudoephedrine, phenylephrine, phenylpropanolamine, epinephrine, norepinephrine, dopamine, and ephedrine); H2 blocking agents (e.g., cimetidine, famotidine, nizatidine, and ranitidine); antihyperlipidemic agents (e.g., clofibrate, cholestyramine, colestipol, fluvastatin, atorvastatin, genfibrozil, lovastatin, niacin, pravastatin, fenofibrate, colesevelam, and simvastatin); antihypercholesterol agents (e.g., lovastatin, simvastatin, pravastatin, fluvastatin, atorvastatin, cholestyramine, colestipol, colesevelam, nicotinic acid, gemfibrozil, and ezetimibe); cardiotonic agents (e.g., digitalis, ubidecarenone, and dopamine); vasodilating agents (e.g., nitroglycerin, captopril, dihydralazine, diltiazem, and isosorbide dinitrate); vasoconstricting agents (e.g., dihydroergotoxine and dihydroergotamine); anticoagulants (e.g., warfarin, heparin, and Factor Xa inhibitors); sedative agents (e.g., amobarbital, pentobarbital, secobarbital, clomethiazole, diphenhydramine hydrochloride, and alprazolam); hypnotic agents (e.g., zaleplon, zolpidem, eszopiclone, zopiclone, chloral hydrate, and clomethiazole); anticonvulsant agents (e.g., lamitrogene, oxycarbamezine, phenytoin, mephenytoin, ethosuximide, methsuccimide, carbamazepine, valproic acid, gabapentin, topiramate, felbamate, and phenobarbital); muscle relaxing agents (e.g., baclofen, carisoprodol, chlorzoxazone, cyclobenzaprine, dantrolene sodium, metaxalone, orphenadrine, pancuronium bromide, and tizanidine); antipsychotic agents (e.g., phenothiazine, chlorpromazine, fluphenazine, perphenazine, prochlorperazine, thioridazine, trifluoperazine, haloperidol, droperidol, pimozide, clozapine, olanzapine, risperidone, quetiapine, ziprasidone, melperone, and paliperidone); antianxiolitic agents (e.g., lorazepam, alprazolam, clonazepam, diazepam, buspirone, meprobamate, and flunitrazepam); antihyperactive agents (e.g., methylphenidate, amphetamine, and dextroamphetamine); antihypertensive agents (e.g., alpha-methyldopa, chlortalidone, reserpine, syrosingopine, rescinnamine, prazosin, phentolamine, felodipine, propanolol, pindolol, labetalol, clonidine, captopril, enalapril, and lisonopril); anti-neoplasia agents (e.g., taxol, actinomycin, bleomycin A2, mitomycin C, daunorubicin, doxorubicin, epirubicin, idarubicin, and mitoxantrone); soporific agents (e.g., zolpidem tartrate, eszopiclone, ramelteon, and zaleplon); tranquilizer agents (e.g., alprazolam, clonazepam, diazepam, flunitrazepam, lorazepam, triazolam, chlorpromazine, fluphenazine, haloperidol, loxapine succinate, perphenazine, prochlorperazine, thiothixene, and trifluoperazine); decongestant agents (e.g., ephedrine, phenylephrine, naphazoline, and tetrahydrozoline); beta blockers (e.g., levobunolol, pindolol, timolol maleate, bisoprolol, carvedilol, and butoxamine); alpha blockers (e.g., doxazosin, prazosin, phenoxybenzamine, phentolamine, tamsulosin, alfuzosin, and terazosin); non-steroidal hormones (e.g., corticotropin, vasopressin, oxytocin, insulin, oxendolone, thyroid hormone, and adrenal hormone); erectile disfunction improvement agents; herbal agents (e.g., glycyrrhiza, aloe, garlic, nigella sativa, rauwolfia, St John's wort, and valerian); enzymes (e.g., lipase, protease, amylase, lactase, lysozyme, and urokinase); humoral agents (e.g., prostaglandins, natural and synthetic, for example, PGE1, PGE2alpha, PGF2alpha, and the PGE1 analog misoprostol); psychic energizers (e.g., 3-(2-aminopropy)indole and 3-(2-aminobutyl)indole); nutritional agents; essential fatty acids; non-essential fatty acids; vitamins; minerals; and combinations thereof.

Any of the above-mentioned APIs may be incorporated in the pharmaceutical composition described herein in any suitable form, such as, for example, as a pharmaceutically acceptable salt, uncharged or charged molecule, molecular complex, solvate or hydrate, prodrug, and, if relevant, isomer, enantiomer, racemic mixture, and/or mixtures thereof. Furthermore, the API may be in any of its crystalline, semi-crystalline, amorphous, or polymorphous forms.

In one embodiment, the API in the pharmaceutical composition may have a potential for abuse. For example, the API may be an opioid analgesic agent, a stimulant agent, a sedative agent, a hypnotic agent, an antianxiolitic agent, or a muscle relaxing agent.

In another embodiment, the API in the pharmaceutical composition may be a combination of an opioid analgesic and a non-opioid analgesic. Suitable opioid and non-opioid analgesics are listed above.

In a further embodiment, the API in the pharmaceutical composition may be a combination of an opioid analgesic and an opioid antagonist, examples of which are listed above.

In a specific embodiment, the API in the pharmaceutical composition may be an opioid analgesic. Exemplary opioid analgesics include oxycodone, oxymorphone, hydrocodone, hydromorphone, codeine, and morphine. In one specific embodiment, the API may be oxycodone hydrochloride. In another specific embodiment, the API may be oxymorphone hydrochloride.

The amount of the API in the pharmaceutical composition can and will vary depending upon the active agent. In embodiments in which the API is an opioid analgesic, the amount of opioid in the pharmaceutical composition may range from about 2 mg to about 160 mg. In various embodiments, the amount of opioid in the pharmaceutical composition may range from about 2 mg to about 10 mg, from about 10 mg to about 40 mg, from about 40 mg to about 80 mg, or from about 80 mg to about 160 mg. In certain embodiments, the amount of opioid in the pharmaceutical composition may be about 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 45 mg, 50 mg, 60 mg, 70 mg, 80 mg, 100 mg, 120 mg, 140 mg, or 160 mg.

In embodiments in which the opioid is oxycodone hydrochloride, the total amount of oxycodone hydrochloride present in the pharmaceutical composition may range from about 2 mg to about 80 mg. In certain embodiments, the amount of oxycodone hydrochloride in the pharmaceutical composition may range from about 2 mg to about 10 mg, from about 10 mg to about 30 mg, or from about 30 mg to about 80 mg. In specific embodiments, the amount of oxycodone hydrochloride present in the pharmaceutical composition may be about 5 mg, about 10 mg, about 15 mg, about 20 mg, about 30 mg, about 40 mg, about 60 mg, or about 80 mg.

In embodiments in which the opioid is oxymorphone hydrochloride, the total amount of oxymorphone hydrochloride present in the pharmaceutical composition may range from about 2 mg to about 80 mg. In certain embodiments, the amount of oxymorphone hydrochloride present in the pharmaceutical composition may range from about 2 mg to about 10 mg, from about 10 mg to about 30 mg, or from about 30 mg to about 80 mg. In specific embodiments, the amount of oxymorphone hydrochloride present in the pharmaceutical composition may be about 5 mg, about 10 mg, about 20 mg, about 30 mg, or about 40 mg.

(vi) Optional Excipients

In various embodiments, the pharmaceutical compositions disclosed herein may further comprise at least one additional pharmaceutically acceptable excipient. Non-limiting examples of suitable excipients include clay minerals, binders, fillers, diluents, disintegrants, chelating agents, flavoring agents, coloring agents, taste masking agents, and combinations thereof.

In one embodiment, the optional excipient may be a clay mineral. A clay mineral refers to a hydrated aluminum phyllosilicate or a hydrated magnesium silicate comprising small insoluble particles. Mixing a clay mineral with a suitable solvent forms a colloidal dispersion of small particles that do not sediment. Non-limiting examples of suitable clay minerals include talc, bentonites, kaolinites, nontronites, montmorillonites, pyrophyllites, saponites, sauconites, vermiculites, and combinations thereof. In one iteration, the clay mineral may be powdered talc or micronized talc.

In a further embodiment, the optional excipient may be a binder. Suitable binders include, but are not limited to, starches, pregelatinized starches, gelatin, polyvinylpyrolidone, cellulose, methylcellulose, sodium carboxymethylcellulose, ethylcellulose, polyacrylamides, polyvinylalcohols, C12-C18 fatty acid alcohols, polyethylene glycols, polyols, saccharides, oligosaccharides, polypeptides, peptides, and combinations thereof.

In another embodiment, the optional excipient may be a filler. Suitable fillers include, without limit, calcium carbonate, calcium phosphate, calcium sulfate, calcium silicate, magnesium carbonate, magnesium oxide, sodium chloride, starch, modified starches, cellulose, microcrystalline cellulose, sucrose, lactose, dextrose, mannitol, sorbitol, talc, and combinations thereof.

In another embodiment, the optional excipient may be a diluent. Non-limiting examples of diluents suitable for use include pharmaceutically acceptable saccharides such as sucrose, dextrose, lactose, microcrystalline cellulose, cellulose, cellulose derivatives, starches, fructose, xylitol, and sorbitol, polyhydric alcohols, pre-manufactured direct compression diluents, and mixtures of any of the foregoing.

In a further embodiment, the optional excipient may be a disintegrant. Examples of suitable disintegrants include, without limit, crospovidone, croscarmellose sodium, sodium carboxymethylcellulose, carboxymethylcellose calcium, sodium starch glycolate, cellulose, microcrystalline cellulose, methylcellulose, silicon dioxide (also called colloidal silicone dioxide), alginates, clays, and combinations of any of the foregoing.

In an alternate embodiment, the optional excipient may be a chelating agent. Non-limiting examples of suitable chelating agents include ethylenediamine tetracetic acid (EDTA) and its salts, N-(hydroxy-ethyl)ethylenediaminetriacetic acid, nitrilotriacetic acid (NIA), ethylene-bis(oxyethylenenitrilo)tetraacetic acid, 1,4,7,10-tetraazacyclodo-decane-N,N',N'',N'''-tetraacetic acid, 1,4,7,10-tetraaza-cyclododecane-N,N',N''-triacetic acid, 1,4,7-tris(carboxymethyl)-10-(2'-hydroxypropyl)-1,4,7,10-tetraazocyclodecane, 1,4,7-triazacyclonane-N,N',N''-triacetic acid, 1,4,8,11-tetraazacyclotetra-decane-N,N',N'',N'''-tetraacetic acid; diethylenetriamine-pentaacetic acid (DTPA), ethylenedicysteine, bis(aminoethanethiol)carboxylic acid, triethylenetetraamine-hexaacetic acid, and 1,2-diaminocyclohexane-N,N,N',N'-tetraacetic acid.

In a further embodiment, the optional excipient may be a flavoring agent. Flavoring agents may be chosen from synthetic flavor oils and flavoring aromatics and/or natural oils, extracts from plants, leaves, flowers, fruits, and combinations thereof.

In still another embodiment, the optional excipient may be a coloring agent. Suitable color additives include food, drug and cosmetic colors (FD&C), drug and cosmetic colors (D&C), or external drug and cosmetic colors (Ext. D&C).

In yet another embodiment, the optional excipient may be a taste-masking agent. Taste-masking materials include, but are not limited to, cellulose ethers, polyethylene glycols, polyvinyl alcohol, polyvinyl alcohol and polyethylene glycol copolymers, monoglycerides or triglycerides, acrylic polymers, mixtures of acrylic polymers with cellulose ethers, cellulose acetate phthalate, and combinations thereof.

The amount of the one or more additional excipients in the pharmaceutical solid dosage form can and will vary depending upon the identity of the excipient and the identities and amounts of the other components of the pharmaceutical composition.

(vii) Optional Film Coating

In embodiments in which the pharmaceutical composition is an oral solid dosage form, the solid dosage form may further comprise a water-soluble film coating. Typically, the film coating comprises at least one hydrophilic polymer, and the coating does not affect the immediate release or abuse deterrent properties of the pharmaceutical composition. The film coating may provide moisture protection, enhanced appearance, increased mechanical integrity, improved swallowability, improved taste, and/or masking of odors.

Film coatings are well known in the art, e.g., some are commercially available under the tradename OPADRY®. Typically, a film coating comprises at least one hydrophilic polymer and at least one plasticizer. Non-limiting examples of suitable polymers include hydroxypropylmethylcellulose, hydroxypropylcellulose, hydroxypropylethylcellulose, ethylcellulose, methylcellulose, cellulose acetate phthalate, microcrystalline cellulose and carrageenan, acrylic polymers, polyvinyl alcohol, anionic and cationic polymers of methacrylic acid, copolymers of methacrylates, copolymers of acrylates and methacrylates, copolymers of ethacrylate and methylmethacrylate, polyvinylacetate phthalate, and shellac. Examples of suitable plasticizers include, without limit, triethyl citrate (TEC), acetyltriethyl citrate (ATEC), acetyl tri-n-butyl citrate (ATBC), dibutyl sebacate, diethyl phthalate, and triacetin. The film coating may optionally comprise additional agents such as a coloring agent, a filler, a flavoring agent, a taste-masking agent, a surfactant, an anti-tacking agent, and/or an anti-foaming agent. Suitable examples of these agents are well known in the art and/or are detailed above.

(viii) Specific Embodiments

In specific embodiments, the pharmaceutical composition comprises from about 5% to about 40% by weight of a non-cellulose polysaccharide chosen from glucomannan, xanthan gum, or combinations thereof; from about 10% to about 50% by weight of a hydrophilic gelling polymer chosen from polyethylene oxide, hydroxypropylmethylcellulose, hydroxypropylcellulose, sodium carboxymethyl cellulose, or combinations thereof; from about 30% to about 60% by weight of an effervescent system comprising an organic acid and an alkali metal bicarbonate; and an API chosen from oxycodone, oxymorphone, hydrocodone, hydromorphone, codeine, or morphine.

(b) Dosage Forms

The physical form of the pharmaceutical composition disclosed herein can and will vary. In general, the pharmaceutical composition is a solid dosage form that is formulated for oral administration. The solid dosage form may be one of various solid dosage units. Non-limiting examples of suitable solid dosage units include tablets, compacts, pellets, caplets, pills, and capsules. Such dosage units may be prepared using conventional methods known to those in the field of pharmaceutical formulation and described in pertinent texts, e.g., in Gennaro, A. R., editor. "Remington: The Science & Practice of Pharmacy", 21st ed., 2006, Williams & Williams, and in the "Physician's Desk Reference", $66^{th}$ ed., 2014, PDR Staff.

In specific embodiments, the solid dosage unit may be a tablet. Non-limiting types of tablets include coated tablets, uncoated tablets, compressed tablets, compacted tablets, molded tablets, layered tablets, bilayer tablets, extruded tablets, multiparticulate tablets, monolithic tablets, and matrix tablets.

In embodiments in which the solid dosage form is a tablet, the tablet generally has a friability of no greater than about 1.0%. In certain embodiments, the tablet may have a friability of less than about 1.0%, less than about 0.5%, less than about 0.3%, less than about 0.2%, less than about 0.1%, less than about 0.05%, or less than about 0.01%. In exemplary embodiments, the tablet has a friability of zero.

(c) In Vitro Release Properties

The pharmaceutical composition disclosed herein is formulated such that the API is released rapidly from the composition. Thus, the composition is termed an immediate release pharmaceutical composition. As used herein, "immediate release" refers to an average release of at least 70% of the API within 45 minutes using a USP approved in vitro release test. Unlike many immediate release compositions, the pharmaceutical composition disclosed herein comprises a blend of high molecular weight non-cellulose polysaccharide(s) and hydrophilic gelling polymer(s). The disclosed composition, however, also comprises an effervescent system that facilitates ready dissolution of the composition and rapid release of the API from the composition.

The in vitro dissolution of the API from the pharmaceutical composition disclosed herein may be measured using an approved USP procedure. For example, dissolution may be measured using an USP approved Type 2 paddle apparatus, at a paddle speed of 50 rpm or 100 rpm, and a constant temperature of 37±0.5° C. The dissolution test may be performed in the presence of 500 mL, 900 mL, or 1,000 mL of a suitable dissolution medium. Non-limiting examples of suitable dissolution media include water, phosphate buffer (pH 6.8), acetate buffer (pH 4.5), and 0.1N HCl.

The pharmaceutical compositions disclosed herein provide immediate release of the API. In some embodiments, the pharmaceutical composition may have an average release of about 50%, 55%, 60%, 65%, 70%, 75%, 80%, 85%, 90%, 95%, or 99% of the API within 45 minutes in the dissolution solution. In other embodiments, the pharmaceutical composition may have an average release of about 50%, 55%, 60%, 65%, 70%, 75%, 80%, 85%, 90%, 95%, or 99% of the API within 30 minutes in the dissolution solution.

(d) Abuse Deterrent Properties

The solid dosage pharmaceutical compositions disclosed herein also have abuse deterrent features. The combination of non-cellulose polysaccharide(s) and hydrophilic gelling polymers along with the effervescent system imparts sufficient mechanical integrity (i.e., strength, hardness, etc.) to a solid dosage composition such the composition is resistant to crushing, grinding, cutting, or pulverizing to form a powder comprising small particles. Additionally, because of the presence of the non-cellulose polysaccharide(s) and the hydrophilic gelling polymer(s), a viscous mixture or gel forms when the solid dosage composition (or fractions thereof) is contacted with a small volume of a suitable solvent at a variety of temperatures.

The mechanical integrity of the solid dosage pharmaceutical composition may be assessed by measuring the hardness or crushing strength of the solid dosage composition. The hardness of the solid dosage composition may be measured using any of numerous hardness testers, which are well known in the art. In general, the solid dosage composition has a hardness or crushing strength of at least 10 kilopond (kp). In various embodiments, the solid dosage composition may have a hardness or crushing strength ranging from about 10 kp to about 20 kp, from about 20 kp to about 30 kp, from about 30 kp to about 40 kp, or more than about 40 kp. In certain embodiments, the hardness or crushing strength of solid dosage composition is less than about 50 kp.

The mechanical integrity of the solid dosage pharmaceutical composition also may be assessed by measuring the particle size distribution after crushing, grinding, or pulverizing the composition in a suitable apparatus for a specified period of time. The solid dosage composition may be ground or milled in a coffee grinder, a spice grinder, a nut grinder, a coffee mill, a blender, a high-shear mill, a ball mill, a co-mill, a pill crusher, a tablet grinder, or another grinding/milling apparatus. In some embodiments, more than about 10%, more than about 20%, more than about 30%, more than about 40%, or more than about 50% of the particles formed when the solid dosage composition is subjected to 6 minutes of milling in a coffee grinder or high shear mill have an average diameter of greater than about 250 microns. In other embodiments, more than about 10%, more than about 20%, more than about 30%, more than about 40%, or more than about 50% of the particles formed when the solid dosage composition is subjected to 3 minutes of milling in a coffee grinder or high shear mill have an average diameter of greater than about 250 microns. Because the solid dosage pharmaceutical composition disclosed herein is resistant to forming a fine powder by crushing, grinding or pulverizing, it deters abuse by inhalation.

Additionally, the solid dosage pharmaceutical composition disclosed herein, whether whole, flattened, broken, crushed, or pulverized, forms a viscous mixture or gel when mixed with a small volume of a suitable solvent at a variety of temperatures. The volume of the suitable solvent may range from about 3 mL to about 15 mL. In some embodiments, the volume may be 5 mL, and in other embodiments, the volume may be 10 mL. Suitable solvents include water, alcohols such as ethanol, acids such as acetic acid, fruit juice, and mixtures of any of the foregoing. The temperature of the extraction may range from about 4° C. to about 100° C. In certain embodiments, the temperature of the extraction may be about room temperature (i.e., about 23-25° C.), about 30° C., about 60° C., or about 90° C. The duration of the extraction may range from about 5 minutes to about 3 hours. In some embodiments, the duration of the extraction may be about 30 minutes or about 60 minutes. The viscosity of the mixture or gel prevents the mixture or gel from being drawn through an injection syringe needle. Consequently, the pharmaceutical compositions disclosed herein are resistant to abuse by extraction, filtering, and/or injection.

(II) Processes for Preparing Solid Dosage Pharmaceutical Compositions

Another aspect of the disclosure encompasses processes for preparing solid dosage forms of the pharmaceutical compositions disclosed herein. The processes comprise: (a) forming a mixture comprising at least one non-cellulose polysaccharide, at least one hydrophilic gelling polymer, and an effervescent system; (b) forming the mixture into a solid dosage unit; and (c) heating the solid dosage unit to form the solid dosage form. The solid dosage form optionally may be scored and optionally may be coated with a water-soluble film coating.

(a) Forming a Mixture

The first step of the process comprises forming a mixture comprising the components of the pharmaceutical composition, which are detailed above in section (I)(a). In general, the mixture comprises at least one API, at least one non-cellulose polysaccharide, at least one hydrophilic gelling polymer, an effervescent system comprising an acid component and a base component, and a lubricant. The components may be combined in any order or may be premixed in various combinations before being combined together. For example, in one embodiment the acid component of the effervescent system may be co-processed with a polyalkylene glycol or poloxamer prior to being mixed with the rest of the components. In another embodiment, the API may be combined with some of the components before being combined with the rest of the components. Thus, a variety of ordered mixing schemes are possible.

The mixture comprising the components of the pharmaceutical composition may be formed by mixing, roller mixing, drum mixing, shear mixing, dry blending, chopping, milling, roller milling, granulating, dry granulating (e.g., slugging or roller compacting), wet granulating (e.g., fluid bed granulating, high shear granulating), and other mixing techniques known in the art.

(b) Forming a Solid Dosage Unit

The process further comprises forming the mixture from step (a) into a solid dosage unit. Suitable solid dosage units are described above in section (I)(b). Means of forming solid dosage units are well known in the art. See, e.g., Gennaro, A. R., editor. "Remington: The Science & Practice of Pharmacy", 21st ed., 2006, Williams & Williams, and in the "Physician's Desk Reference", $66^{th}$ ed., 2014, PDR Staff. In specific embodiments, the solid dosage unit may be a tablet. The tablet may be a compression tablet, a molded tablet, a compacted tablet, or a pressed tablet. In exemplary embodiments, the tablet may be formed by direct compression. The shape of the tablet may vary. Non-limiting tablet shapes include round, oval, rectangular, and triangular. The size and mass of the tablet may vary. In various embodiments, the mass of the tablet may be range from about 100 mg to about 1000 mg. In exemplary embodiments, the mass of the tablet may range from about 300 mg to about 500 mg. The solid dosage unit may be scored by selecting the appropriate dies and/or punches.

(c) Heating the Solid Dosage Unit

The process further comprises heating the solid dosage unit from step (b). This heating step dries and cures the solid dosage unit, wherein the cured solid dosage form may have improved properties or characteristics relative to an uncured solid dosage unit. For example, the heating step may remove water from the solid dosage form, thereby protecting the effervescent system from premature effervescence. Additionally, the heating step may plasticize some of the polymers, thereby leading to increased resistance to crushing/pulverization and/or to more rapid release of the API.

In general, the heating step occurs at a temperature of less than about 90° C. In various embodiments, the solid dosage unit may be heated at a temperature from about 30° C. to about 35° C., from about 35° C. to about 40° C., from about 40° C. to about 45° C., from about 45° C. to about 50° C., from about 50° C. to about 55° C., from about 55° C. to about 60° C., from about 60° C. to about 65° C., from about 65° C. to about 70° C., from about 70° C. to about 75° C., from about 75° C. to about 80° C., from about 80° C. to about 85° C., or from about 85° C. to about 90° C. In specific embodiments, the heating temperature may range from about 50° C. to about 85° C.

The duration of the heating step can and will vary depending upon the components of the composition and the heating temperature. The duration of the heating step may range from about 10 minutes to about 20 hours. In some embodiments, the duration of the heating step may range from about 10 to about 60 minutes, from about 1 to about 2 hours, from about 2 to about 3 hours, from about 3 to about 5 hours, from about 5 to about 10 hours, or from about 10 to about 20 hours. In general, the higher the temperature, the shorter the duration of time for heating.

In specific embodiments, the solid dosage unit may be heated to a temperature from about 65° C. to about 80° C. for a period of time ranging from about 1 hour to about 3 hours.

(d) Optionally Coating the Solid Dosage Form

The solid dosage form may be coated with a film coating. Suitable film coatings are detailed above in section (I)(a) (viii). The optional coating may be applied to the solid dosage unit prior to the heating step, or the optional coating may be applied to the solid dosage form after the heating step.

Definitions

When introducing components of the embodiments described herein, the articles "a", "an", "the" and "said" are intended to mean that there are one or more of the elements. The terms "comprising", "including" and "having" are intended to be inclusive and mean that there may be additional components other than the listed components.

If the components described herein have asymmetric centers, all chiral, diastereomeric, racemic forms and all geometric isomeric forms of a structure are intended, unless the specific stereochemistry or isomeric form is specifically indicated.

As used herein, "abuse deterrent" refers to any property or feature of a pharmaceutical composition that lessens the potential for abuse of the active ingredient(s) in the composition.

The terms "gum" or "natural gum" refer to water-soluble and/or water-swellable polysaccharides derived from natural sources, or structurally modified derivatives thereof, which are capable of forming highly viscous gels even at low concentrations.

The term "hydrophilic gelling polymer" refers to a polymer with affinity for water such that it readily absorbs water or an aqueous solution and/or swells when in contact with water or an aqueous solution to form a viscous mixture or gel.

As used herein, "immediate release" refers to an average release of at least 70% of the API within 45 minutes using a USP approved in vitro release procedure.

Having described the invention in detail, it will be apparent that modifications and variations are possible without departing from the scope of the invention defined in the appended claims.

EXAMPLES

The following examples are included to illustrate, but not to limit the claimed pharmaceutical compositions and processes for making.

Example 1: Preparation of Formulations 1-3

A 50 g batch of each formulation presented below in Table 1 was prepared by combining all the components except magnesium stearate in a plastic bag and manually blending the mixture for 5 minutes. The magnesium stearate was then added and the mixture was blended for an additional 2-3 minutes. The blends were then compressed into oval tablets using a single-station Natoli tablet press at a compression force of about 21 kN. The tablets were placed in an aluminum pan and cured in a laboratory oven by heating at 80° C. for 3 hours.

TABLE 1

Compositions of Formulations 1, 2, and 3

| Ingredient | Formulation 1 mg/tablet | Formulation 1 % w/w | Formulation 2 mg/tablet | Formulation 2 % w/w | Formulation 3 mg/tablet | Formulation 3 % w/w |
|---|---|---|---|---|---|---|
| Oxycodone HCl | 30.84 | 6.56 | 30.84 | 6.17 | 30.84 | 5.51 |
| L-(+)-Tartaric acid, extra fine | 122.00 | 25.96 | 122.00 | 24.40 | 122.00 | 21.79 |
| PEG 3350 | 7.05 | 1.5 | 7.05 | 1.41 | 7.05 | 1.26 |
| Effer-Soda ® 12 | 104.00 | 22.13 | 104.00 | 20.80 | 104.00 | 18.57 |
| Polyox N10 LEO (100K) | 103.40 | 22.00 | 103.40 | 20.68 | 103.40 | 18.46 |
| Butylated hydroxytoluene | 0.06 | 0.013 | 0.06 | 0.012 | 0.06 | 0.011 |
| Citric acid, anhydrous | 4.70 | 1.00 | 4.70 | 0.94 | 4.70 | 0.84 |
| Polyox WSR 301 NF LEO (4 million) | 4.25 | 0.90 | 4.25 | 0.85 | 4.25 | 0.76 |
| Glucomannan | 90.60 | 19.28 | 120.60 | 24.12 | 120.60 | 21.54 |
| Klucel HF (HPC) (1.15 million) | 0 | 0 | 0 | 0 | 60.00 | 10.71 |
| Magnesium stearate | 3.10 | 0.66 | 3.10 | 0.62 | 3.10 | 0.55 |
| Total | 470.00 | 100.00 | 500.00 | 100.00 | 560.00 | 100.00 |

Example 2: Dissolution Analysis of Formulations 1-3

The in vitro release of oxycodone hydrochloride was determined using an USP approved test. The dissolution parameters were: USP Apparatus Type 2 (paddles), 50 rpm, and 500 mL water or 0.1 N HCl, at 37°±0.5° C. The amount of oxycodone HCl in the dissolution fluid was determined at regular intervals. The dissolution data are presented in Tables 2 and 3. All three formulations exhibited immediate release of the active ingredient.

TABLE 2

Dissolution of Tablets in Water - Formulations 1 and 2

| | % Oxycodone HCl Dissolved | | | |
|---|---|---|---|---|
| | Formulation 1 | | Formulation 2 | |
| Time (minutes) | Uncured Tablet | Cured Tablet | Uncured Tablet | Cured Tablet |
| 5 | 67.0 | 65.6 | 73.7 | 63.6 |
| 10 | 89.0 | 88.7 | 86.6 | 89.1 |
| 15 | 90.2 | 90.6 | 89.0 | 91.2 |
| 20 | 90.6 | 90.7 | 89.5 | 91.4 |
| 30 | 90.4 | 91.0 | 89.5 | 90.9 |
| 45 | 90.0 | 90.3 | 90.3 | 92.0 |

TABLE 3

Dissolution of Cured Tablets in 0.1N HCl - Formulations 2 and 3

| Time (minutes) | % Oxycodone HCl Dissolved | |
|---|---|---|
| | Formulation 2 | Formulation 3 |
| 5 | 70.6 | 49.9 |
| 10 | 95.3 | 81.6 |
| 15 | 97.0 | 95.4 |
| 20 | 96.9 | 97.4 |
| 30 | 96.6 | 97.5 |
| 45 | 98.2 | 97.5 |

Example 3: Abuse Deterrence Tests—Crushing

Cured tablets from Formulations 1-3 were milled under high-shear conditions with a Cuisinart DCG-20N coffee grinder. The grinder was paused for 30 seconds after each 30 seconds of milling for a total milling time of 3 minutes (i.e., six pulses of 30 seconds). The milled products were characterized by particle size analysis. Table 4 presents the particle size data from the milling experiments, with the particle size reported as greater than 500 µm, from 250-500 µm, and less than 250 µm. In general, particles greater than 250 μm are considered difficult to snort, and hence, formulations resulting in a large fraction of particles greater than 250 μm are assumed to have better deterrence against this route of abuse.

TABLE 4

Particle Size Distribution of Cured Tablets - Formulations 1-3

| | Weight fraction | | |
|---|---|---|---|
| | >500 μm | 250-500 μm | <250 μm |
| Formulation 1 | 4.1 | 25.8 | 62.9 |
| Formulation 2 | 3.3 | 26.7 | 66.6 |
| Formulation 3 | 2.4 | 23.1 | 72.7 |

Example 4: Abuse Deterrence Tests—Extraction with Solvents

Tablets from Formulations 1-3 were tested to determine how much oxycodone could be extracted with various solvents and at various temperatures. The less active ingredient that is extracted, the better deterrence provided by the formulation against abuse IV administration.

In one test, cured tablets from Formulations 2 and 3 were cut into 8 pieces with a razor blade and the resultant pieces were extracted (no stirring) with 5 mL or 10 mL of water or 95% ethanol for 30 minutes at room temperature, 60° C., or 90° C. At the end of the extraction period, the supernatant liquid was filtered through a cotton plug into a syringe. The amount of oxycodone HCl in the extract was determined by HPLC and expressed as a fraction of the total amount of oxycodone HCl in the tablets. The results are shown in Table 5.

TABLE 5

Extraction Data from Cut Tablets - Formulations 2 and 3

| Sample | Extraction Solvent | Extraction Temperature | Extraction Volume (mL) | Volume Recovered (mL) | Amount of Oxycodone Extracted | |
|---|---|---|---|---|---|---|
| | | | | | mg | % (in theory) |
| F2 | Water | Room Temp | 5 | 1.1 | 6.4 | 21.2 |
| F3 | Water | Room Temp | 5 | 0.6 | 4.0 | 13.4 |
| F2 | Water | Room Temp | 10 | 3.3 | 8.7 | 29.1 |
| F3 | Water | Room Temp | 10 | 1.4 | 4.1 | 13.7 |
| F2 | 95% EtOH | Room Temp | 5 | 3.1 | 5.4 | 17.9 |
| F3 | 95% EtOH | Room Temp | 5 | 3.1 | 3.0 | 10.0 |
| F2 | 95% EtOH | Room Temp | 10 | 7.1 | 7.1 | 23.8 |
| F3 | 95% EtOH | Room Temp | 10 | 7.1 | 4.0 | 13.5 |
| F2 | Water | 90° C. | 5 | 0.6 | 2.4 | 7.9 |
| F3 | Water | 90° C. | 5 | 0.9 | 3.1 | 10.3 |
| F2 | Water | 90° C. | 10 | 4.4 | 11.8 | 39.3 |
| F3 | Water | 90° C. | 10 | 3.6 | 9.7 | 32.3 |
| F2 | 95% EtOH | 60° C. | 5 | 3.1 | 9.0 | 29.9 |
| F3 | 95% EtOH | 60° C. | 5 | 2.9 | 7.6 | 25.4 |
| F2 | 95% EtOH | 60° C. | 10 | 7.2 | 9.0 | 30.2 |
| F3 | 95% EtOH | 60° C. | 10 | 6.8 | 6.4 | 21.3 |

In another test, cured tablets from Formulations 1, 2, and 3 were milled into particles as described above and the particles were extracted (no stirring) with 10 mL of water or 95% ethanol for 30 minutes at room temperature, 60° C., or 90° C. At the end of the extraction period, the supernatant liquid was filtered through a cotton plug into a syringe. The amount of oxycodone HCl in the extract was determined by HPLC and expressed as a fraction of the total amount of oxycodone HCl in the tablets. The results are shown in Table 6.

TABLE 6

Extraction Data from Pulverized Tablets - Formulations 1-3

| Sample | Extraction Solvent | Extraction Temperature | Volume Recovered (mL) | Amount of Oxycodone Extracted | |
|---|---|---|---|---|---|
| | | | | mg | % (in theory) |
| F1 | Water | Room Temp | 7.8 | 11.21 | 37.4 |
| F2 | Water | Room Temp | 6.0 | 7.99 | 26.6 |
| F3 | Water | Room Temp | 6.5 | 6.18 | 20.6 |
| F1 | 95% EtOH | Room Temp | 7.0 | 4.39 | 14.6 |
| F2 | 95% EtOH | Room Temp | 6.9 | 5.76 | 19.2 |
| F3 | 95% EtOH | Room Temp | 6.3 | 7.40 | 24.7 |
| F1 | Water | 90° C. | 8.2 | 17.40 | 58.0 |
| F2 | Water | 90° C. | 8.2 | 12.24 | 40.8 |
| F3 | Water | 90° C. | 8.1 | 9.50 | 31.7 |
| F1 | 95% EtOH | 60° C. | 7.0 | 8.05 | 26.8 |
| F2 | 95% EtOH | 60° C. | 7.0 | 10.02 | 33.4 |
| F3 | 95% EtOH | 60° C. | 4.5 | 9.05 | 30.2 |

Example 5: Preparation of Formulations 4 and 5

Formulations were prepared, tableted, and cured essentially as described in Example 1 using the ingredients listed in Table 7.

TABLE 7

Compositions of Formulations 4 and 5

| | Formulation 4 | | Formulation 5 | |
|---|---|---|---|---|
| Ingredient | mg/tablet | % w/w | mg/tablet | % w/w |
| Oxycodone HCl | 30.84 | 6.43 | 30.84 | 6.17 |
| L-(+)-Tartaric acid, extra fine | 122.00 | 25.42 | 122.00 | 24.40 |
| PEG 3350 | 7.05 | 1.47 | 7.05 | 1.41 |
| Effer-Soda ® 12 | 104.00 | 21.67 | 104.00 | 20.80 |
| Polyox N10 LEO (100K) | 103.40 | 21.54 | 103.40 | 20.68 |
| Butylated hydroxytoluene | 0.06 | 0.01 | 0.06 | 0.01 |
| Citric acid, anhydrous | 4.70 | 0.98 | 4.70 | 0.94 |
| Polyox WSR 301 NF LEO (4M) | 4.25 | 0.89 | 4.25 | 0.85 |
| Glucomannan | 40.00 | 8.33 | 60.00 | 12.00 |
| Sodium carboxymethylcellulose (30K) | 20.00 | 4.17 | 20.00 | 4.00 |
| Methocel K100M CR (250K) | 30.00 | 6.25 | 30.00 | 6.00 |
| Xanthan gum (Vanzan NF) | 10.60 | 2.21 | 10.60 | 2.12 |
| Magnesium stearate | 3.10 | 0.65 | 3.10 | 0.62 |
| Total | 480.00 | 100.00 | 500.00 | 100.00 |

Example 6: Abuse Deterrence Tests—Extraction with Solvents

Cured tablets from Formulations 4 and 5 were cut into 8 pieces with a razor blade and the resultant pieces were extracted (no stirring) with 5 mL or 10 mL of water or 95% ethanol for 30 minutes at room temperature, 60° C., or 90° C. At the end of the extraction period, the supernatant liquid was filtered through a cotton plug into a syringe. The amount of oxycodone HCl in the extract was determined by HPLC and expressed as a fraction of the total amount of oxycodone HCl in the tablets. The results are shown in Table 8.

TABLE 8

Extraction Data from Cut Tablets - Formulations 4 and 5

| Sample | Extraction Solvent | Extraction Temperature | Extraction Volume (mL) | Volume Recovered (mL) | Amount of Oxycodone Extracted mg | % (in theory) |
|---|---|---|---|---|---|---|
| F4 | Water | Room Temp | 5 | 0.9 | 3.1 | 10.3 |
| F5 | Water | Room Temp | 5 | 0.9 | 2.4 | 8.1 |
| F4 | Water | Room Temp | 10 | 2.9 | 6.4 | 21.2 |
| F5 | Water | Room Temp | 10 | 3.4 | 5.7 | 18.9 |
| F4 | 95% EtOH | Room Temp | 5 | 3.1 | 5.3 | 17.8 |
| F5 | 95% EtOH | Room Temp | 5 | 3.1 | 4.7 | 15.8 |
| F4 | 95% EtOH | Room Temp | 10 | 7.2 | 6.4 | 21.2 |
| F5 | 95% EtOH | Room Temp | 10 | 7.1 | 5.3 | 17.7 |
| F4 | Water | 90° C. | 5 | 1.5 | 5.6 | 18.8 |
| F5 | Water | 90° C. | 5 | 1.5 | 3.3 | 11.1 |
| F4 | Water | 90° C. | 10 | 5.7 | 10.6 | 35.4 |
| F5 | Water | 90° C. | 10 | 4.9 | 10.3 | 34.4 |
| F4 | 95% EtOH | 60° C. | 5 | 3.2 | 9.0 | 30.1 |
| F5 | 95% EtOH | 60° C. | 5 | 3.2 | 8.2 | 27.4 |
| F4 | 95% EtOH | 60° C. | 10 | 7.2 | 9.4 | 31.4 |
| F5 | 95% EtOH | 60° C. | 10 | 7.0 | 9.8 | 32.8 |

What is claimed is:

1. A process for preparing a solid dosage form, the process comprising:
   (a) blending at least one active pharmaceutical ingredient (API) or pharmaceutically acceptable salt thereof, about 10% w/w to about 25% w/w of at least one natural gum comprising glucomannan, about 25% w/w to about 35% w/w of a combination of hydrophilic gelling polymers comprising (i) at least one cellulose ether, (ii) a polyethylene oxide having an average molecular weight of about 100,000, and (iii) a polyethylene oxide having an average molecular weight of about 4,000,000, and about 40% w/w to about 50% w/w of an effervescent system to form a mixture;
   (b) compressing the mixture into a solid dosage unit; and
   (c) heating the solid dosage unit at a temperature from about 50° C. to less than about 90° C. for 1 to 3 hours to form the solid dosage form;
   wherein the solid dosage form deters abuse and provides immediate release of the at least one API.

2. The process of claim 1, wherein the at least one API is an opioid or a combination of an opioid and a non-opioid analgesic, and the opioid is oxycodone, oxymorphone, hydrocodone, hydromorphone, codeine, or morphine.

3. The process of claim 1, wherein the at least one natural gum comprising glucomannan further comprises xanthan gum.

4. The process of claim 1, wherein the at least one cellulose ether is hydroxypropylmethylcellulose, hydroxypropylcellulose, sodium carboxymethylcellulose, or a combination thereof.

5. The process of claim 1, wherein the effervescent system comprises a) an acid component chosen from an organic acid, an inorganic acid, or a combination thereof, and b) a base component chosen from an alkali metal bicarbonate, an alkaline earth metal bicarbonate, an alkali metal carbonate, an organic carbonate, or a combination thereof.

6. The process of claim 1, wherein the mixture at step (a) further comprises a lubricant, and the lubricant is present in an amount of less than about 1% by weight of the solid dosage form.

7. The process of claim 1, further comprising applying a film coating to the solid dosage unit before step (c) or applying a film coating to the solid dosage form after step (c).

8. The process of claim 1, wherein the solid dosage form is a tablet, compact, pellet, caplet, or pill.

* * * * *